United States Patent
Baumgart (10) Patent No.: US 10,136,996 B2
(45) Date of Patent: Nov. 27, 2018

(54) IMPLANTABLE PROSTHESIS FOR REPLACING THE HUMAN KNEE JOINT

(71) Applicant: Rainer Baumgart, Munich (DE)

(72) Inventor: Rainer Baumgart, Munich (DE)

( * ) Notice: Subject to any disclaimer, the term of this patent is extended or adjusted under 35 U.S.C. 154(b) by 39 days.

(21) Appl. No.: 15/076,841

(22) Filed: Mar. 22, 2016

(65) Prior Publication Data

US 2017/0056186 A1    Mar. 2, 2017

(30) Foreign Application Priority Data

Aug. 31, 2015  (EP) .................................... 15183120

(51) Int. Cl.
 *A61F 2/38*    (2006.01)
 *A61B 17/72*   (2006.01)
 (Continued)

(52) U.S. Cl.
 CPC .......... *A61F 2/384* (2013.01); *A61B 17/7216* (2013.01); *A61F 2/389* (2013.01);
 (Continued)

(58) Field of Classification Search
 CPC ...... A61F 2/3836; A61F 2/384; A61F 2/3854; A61F 2/3859; A61F 2/389;
 (Continued)

(56) References Cited

U.S. PATENT DOCUMENTS 5,180,383 A *   1/1993 Haydon ............. A61B 17/1764
                                                   606/300
2009/0306784 A1* 12/2009 Blum ................. A61B 17/1714
                                                   623/20.21

FOREIGN PATENT DOCUMENTS

EP    1216669 A2    6/2002
EP    1371346 A1   12/2003
 (Continued)

OTHER PUBLICATIONS

European Search Report, European Patent Application No. 15183120.3, dated Feb. 10, 2016.

*Primary Examiner* — Thomas J Sweet
*Assistant Examiner* — Megan Wolf
(74) *Attorney, Agent, or Firm* — Marshall, Gerstein & Borun LLP (57) ABSTRACT

The implantable prosthesis for replacing a human knee joint comprises a femoral prosthetic element (12) and a tibial prosthetic element (14) which are articulated with one another by means of a joint device (30) for the purpose of executing a knee bend. The tibial prosthetic element (14) has a through-opening (40) for the passage of a tool (84), a rod-like shaft anchoring part (32) or an intramedullary lengthening nail (80). In order to reduce the extent of a surgical intervention and thus the risk of infection also for the lengthening of the tibia, the joint device (30) is designed such that it forms a guide channel (42) for the passage of the tool (84), the rod-like shaft anchoring part (32) or the intramedullary lengthening nail (80) from the outside, which guide channel is in alignment with the through-opening (40) and is in connection therewith when the tibial prosthetic element (14) and the femoral prosthetic element (12) are arranged at a predetermined angle relative to one another in a functional position corresponding to a knee bend.

18 Claims, 6 Drawing Sheets

(51) Int. Cl.
    *A61F 2/28*     (2006.01)
    *A61F 2/30*     (2006.01)
    *A61F 2/48*     (2006.01)
    *A61B 17/00*    (2006.01)

(52) U.S. Cl.
    CPC .......... *A61F 2/3836* (2013.01); *A61F 2/3845* (2013.01); *A61F 2/3854* (2013.01); *A61F 2/3859* (2013.01); *A61B 17/72* (2013.01); *A61B 2017/00411* (2013.01); *A61F 2002/2825* (2013.01); *A61F 2002/3055* (2013.01); *A61F 2002/30706* (2013.01); *A61F 2002/482* (2013.01)

(58) Field of Classification Search
    CPC ...... A61F 2002/4243; A61F 2002/4246; A61F 2002/4248
    See application file for complete search history.

(56) References Cited

FOREIGN PATENT DOCUMENTS

| | | |
|---|---|---|
| EP | 2468216 A1 | 6/2012 |
| JP | 2011139785 A | 7/2011 |
| WO | WO-2008/000496 A2 | 1/2008 |

\* cited by examiner

IMPLANTABLE PROSTHESIS FOR REPLACING THE HUMAN KNEE JOINT

CROSS-REFERENCE TO RELATED APPLICATIONS

This application claims the benefit of EP Patent Application No. 15 183 120.3 filed on Aug. 31, 2015. The entirety of the foregoing application is incorporated by reference herein.

FIELD OF THE DISCLOSURE

The disclosure relates to an implantable prosthesis for replacing the human knee joint, and optionally also the adjoining bone portions, and more particularly to a prosthesis having a femoral prosthetic element and a tibial prosthetic element which are articulated with one another by means of a joint device for the purpose of executing a knee bend, the tibial prosthetic element including a through-opening for the passage of a tool, a rod-shaped shaft anchoring part, or an intramedullary lengthening nail. The prosthesis is preferably used following resection of a bone tumor.

BACKGROUND

Malignant knee tumors are frequently located in the femur or in the tibia close to the knee joint so that, after removal of the affected bone portion, part of the shaft as well as the associated femoral or tibial joint section must be replaced by artificial prosthetic elements.

In any case, a prosthetic part must also be implanted in the corresponding bones in order to achieve articulation and coupling with the prosthetic element of the affected bone. Coupling is by means of a joint device such as a hinge or ball mechanism, which allows mobility between the femur and the tibia that is as close as possible to the natural mobility of the knee joint. The prosthesis is anchored in the femur and in the tibia in each case by means of a shaft anchoring means introduced into the bone. If later removal is intended, the shaft anchoring means can be formed so as to have a smooth surface so that bone does not grow into it. If definitive anchoring is intended, the surface can be roughened or coated so that bone tissue is able to grow into it. Alternatively, the shaft anchoring means can also be fixed by means of bone cement.

Since malignant bone tumors frequently occur during the growth phase, the loss of the growth plate on the affected side and continued growth on the opposite side result in a leg length discrepancy following surgical removal of the tumor and the implanting of a tumor prosthesis. The retarded growth affects primarily the bone affected by the tumor itself but also the corresponding bone, that is to say, if the tumor was located in the femur, for example, growth not only of the femur but also of the tibia is retarded. Even if the shaft anchoring part of the tibia is in this case smooth and polished so that the bone can in principle continue to grow, there is thus a growth retardation also in the corresponding bone, which contributes to the developing leg length discrepancy.

Possibilities for lengthening the bone affected by the tumor are known from EP 1 371 346 A1 and EP 2 468 216 A1. To that end, EP 1 371 346 A1 discloses, by means of the prosthesis, exchanging the shaft anchoring means in the remaining bones for an intramedullary lengthening nail which, following an osteotomy, slowly pulls the two bone fragments apart so that new bone tissue can form in the growing gap (callus distraction method). When the tumor is located in the proximal femur, the exchange is likewise made proximally, and when the tumor is located in the distal femur, the exchange is likewise made distally, decoupling of the prosthesis not being absolutely essential from an anatomical point of view because the point of entry can be reached axially with the knee bent for tools and the shaft anchoring parts or also an intramedullary distraction nail. When the tumor is located in the proximal tibia, the tibial anchoring means cannot be exchanged either with the knee extended or with the knee bent without decoupling the prosthetic elements, because the axial access is covered by the femoral prosthetic element.

EP 2 468 216 A1 discloses for the first time a solution for exchanging the shaft anchoring means in the femur by a minimally invasive operating technique by changing the components from the opposite end of the bone. Accordingly, if the tumor is located in the femur and there is no length discrepancy in the lower leg, a further major intervention via the prosthesis can be avoided by means of a prosthesis according to EP 2 468 216 A1, and the risk of infection can thus be reduced significantly.

Where the tibia requires lengthening, either following a primary tumor of the tibia or if the tibia is also shortened following a tumor located in the femur, and the temporary shaft anchoring means in the tibia is therefore to be exchanged for an intramedullary lengthening nail and, when growth is complete, the intramedullary lengthening nail is to be exchanged for a coated shaft anchoring means which grows permanently into the bone, the prosthesis must be decoupled each time, which requires a major surgical intervention having a considerable risk of infection.

The advantage described in EP 2 468 216 A1 thus ultimately comes to bear only if there is not a shortening of the lower leg at the same time, since the solution described in EP 2 468 216 A1 cannot be applied to the lower leg. However, for the frequent case that the shortening also affects the lower leg, as already mentioned, there is as yet no possibility for carrying out a lengthening of the type described in EP 1 371 346 A1 by a minimally invasive technique without decoupling the prosthesis. Accordingly, the advantageous possibilities of leg length equalization on the opposite side by bone growth continue to be accompanied by the considerable risk of infection due to repeated major surgical interventions in the region of the prosthesis.

Accordingly, an aim of the present disclosure is to reduce the extent of further surgical interventions and thus the risk of infection also for lengthening the tibia, while retaining the advantages of bone lengthening by the callus distraction method.

SUMMARY

The aim is believed to be achieved by an implantable prosthesis having a femoral prosthetic element and a tibial prosthetic element which are articulated with one another by means of a joint device for the purpose of executing a knee bend. The tibial prosthetic element may have a through-opening for the passage of a tool, a rod-like tibial shaft anchoring part, or an intramedullary lengthening nail. The joint device may form a guide channel for the passage of the tool, the rod-like tibial shaft anchoring part, or the intramedullary lengthening nail from the outside. The guide channel may be in alignment with the through-opening and may be in connection therewith when the tibial prosthetic element and the femoral prosthetic element are arranged at a predetermined angle relative to one another in a functional position corresponding to a knee bend. Additional optional advantageous developments of the prosthesis are also provided.

In a preferred embodiment of the disclosure, both the tibial prosthetic element and the femoral prosthetic element have through-openings and the joint device has a passageway, through which both tools, for example a bone cutter, and an intramedullary lengthening nail or a smooth or coated shaft anchoring means can be introduced proximally into the tibial shaft. The passage through the joint device, by means of which the two prosthetic elements are articulated with one another, is so designed that a guide channel which is in alignment with the through-opening and is in connection therewith passes through or past it when the tibial prosthetic element and the femoral prosthetic element are arranged at a predetermined angle to one another in a functional position corresponding to a knee bend. The angle is determined in such a way that both different tools and an intramedullary lengthening nail or a shaft anchoring means can be introduced into the tibial shaft via a small suprapatellar skin incision of approximately 2 cm in length.

Since the femoral prosthetic element has sufficient width before it merges into the shaft, the guide channel does not lead to excessive weakening and can be covered flush and smoothly relative to the surface by a plastics insert in the region of the patellar groove.

In order to align the through-opening in the tibial prosthetic element with the guide channel in the femoral prosthetic element, a knee bend from 20° to 90°, preferably from 30° to 60°, particularly preferably from 30° to 45°, is required. The joint device between the femoral prosthetic element and the tibial prosthetic element is either constructed such that the through-opening aligns itself when the joint bends as intended, or alignment takes place by the intervention of a tool via the suprapatellar access or an additional stab incision, in which a temporary blockade of the joint device is brought about.

The joint device preferably includes a joint head which is connected to the femoral prosthetic element and has an interior space in which a joint element connected to the tibial prosthetic element is guided in a pivotable and optionally also slightly rotatable manner in order to guide the knee bend, there being formed in the joint head a passage which opens into the interior space and in the joint element a passageway, for example a through-bore, which, in the functional position, are in alignment with one another to form a guide channel with the passage in the tibial prosthetic element.

The femoral prosthetic element can consist in a modular manner of a shaft replacement of variable length, if the tumor was located in the femur, and a joint head or can also form a part. The tibial prosthetic element can likewise consist in a modular manner of a shaft replacement of variable length, if the tumor was located in the tibia, and the joint element or can form a part.

A guide sleeve can be introduced via a suprapatellar access, which guide sleeve facilitates the exchange of tools, intramedullary distraction nails or shaft anchoring means while protecting the tissue. Advantageously, the guide sleeve can also be placed in the femoral prosthetic element in an interlocking manner and fixed by means of a cone, a bayonet or a thread.

In order to secure the position of the passage and of the through-bore for the exchange and to stabilize the knee joint in that position, the sleeve can also be placed further into the joint device or into the tibial prosthetic element, where it can advantageously be fixed in a force-locking or interlocking manner by means of a cone, a bayonet or a thread.

If the joint device is in the form of a hinge having a hinge axis, the hinge axis can either be split in two or can have in the middle region a bore or a recess of a sufficient size. If it is a joint device that is connected to the femoral or tibial prosthetic element and has, for example, the form of a ball, the guide channel can run centrally or non-centrally through the joint device, for example through or past the ball and the fixing elements thereof.

The tibial prosthetic element as already disclosed in EP 2 468 216 A1 is preferably provided with a transverse bore which opens into the cavity and through which a cable or a hose can be guided, which cable or hose can be connected at one end to an energy supply, for example a subcutaneous antenna, and at the other end to the drive of an intramedullary distraction nail, if an intramedullary distraction nail is inserted into the tibial prosthetic element after removal of the shaft anchoring part, in order to perform a bone distraction by the callus distraction method.

The shaft anchoring part can be a solid, smooth or coated stabilizer or an intramedullary nail with an integrated drive for distraction of the bone.

After resection of a tumor in the distal femur in growing children, the femoral prosthetic element, which replaces part of the shaft, depending on the size of the tumor, is implanted first. Depending on the required length, the prosthetic element can consist of one component or also in a modular manner of a plurality of components. The corresponding prosthetic element is implanted in the tibia by first introducing a polished shaft through the through-opening into the tibia shaft, so that further growth is possible.

After resection of a tumor in the proximal tibia in growing children, the tibial prosthetic element, which likewise replaces part of the shaft, depending on the size of the tumor, is first implanted, it being possible in this case too for the prosthetic element to consist of one component or also in a modular manner of a plurality of components, depending on the required length. In this case too, the corresponding prosthetic element is implanted in the femur by first introducing a polished shaft, so that further growth is possible.

Where there is a need for lengthening owing to growth of the opposite side, it is thus possible according to the prior art, as disclosed in patents 1 371 346 A1 or patent EP 2 468 216 A1, to exchange the shaft anchoring means in the femur for an intramedullary distraction nail without decoupling the prosthesis. If the present application is used as intended, the temporary shaft anchoring means of the tibial prosthetic element can now likewise be exchanged and optionally replaced, for example by an intramedullary distraction nail, without decoupling the prosthesis.

To that end, the knee joint is placed at a predetermined angle which, starting from an extended position, is preferably approximately from 30° to 45°. Via a small skin incision above the patella, after longitudinal incision of the quadriceps tendon, a dilator is introduced which cleaves a tunnel through the soft parts to the femoral prosthetic element. A guide sleeve can then preferably be fed via the dilator and anchored in the femoral prosthetic element by interlocking or a force-locking connection. If the coupling mechanism does not align itself automatically, alignment and optionally also temporary fixing between the femoral and tibial prosthetic element and optionally also to the joint device are carried out either under visual guidance using an image converter or by means of a suitable tool via a stab incision, for example using a metal pin. In order to fix the functional position of the knee joint, the guide sleeve can in further embodiments also be fed through the femoral prosthetic element into the joint device or even further into the tibial prosthetic element. Via the portal thus formed, the temporary shaft anchoring means of the tibial prosthetic element can first be removed, and cutting tools can then be used or an intramedullary distraction nail can be implanted. In the same minimally invasive manner, intramedullary distraction nails can be exchanged if repeated lengthening is required and can be replaced at the end of the lengthening phase by a definitive, preferably coated shaft anchoring means.

The disclosure will be explained in greater detail with reference to drawings, in which.

BRIEF DESCRIPTION OF THE DRAWINGS

DETAILED DESCRIPTION

Figure 1:
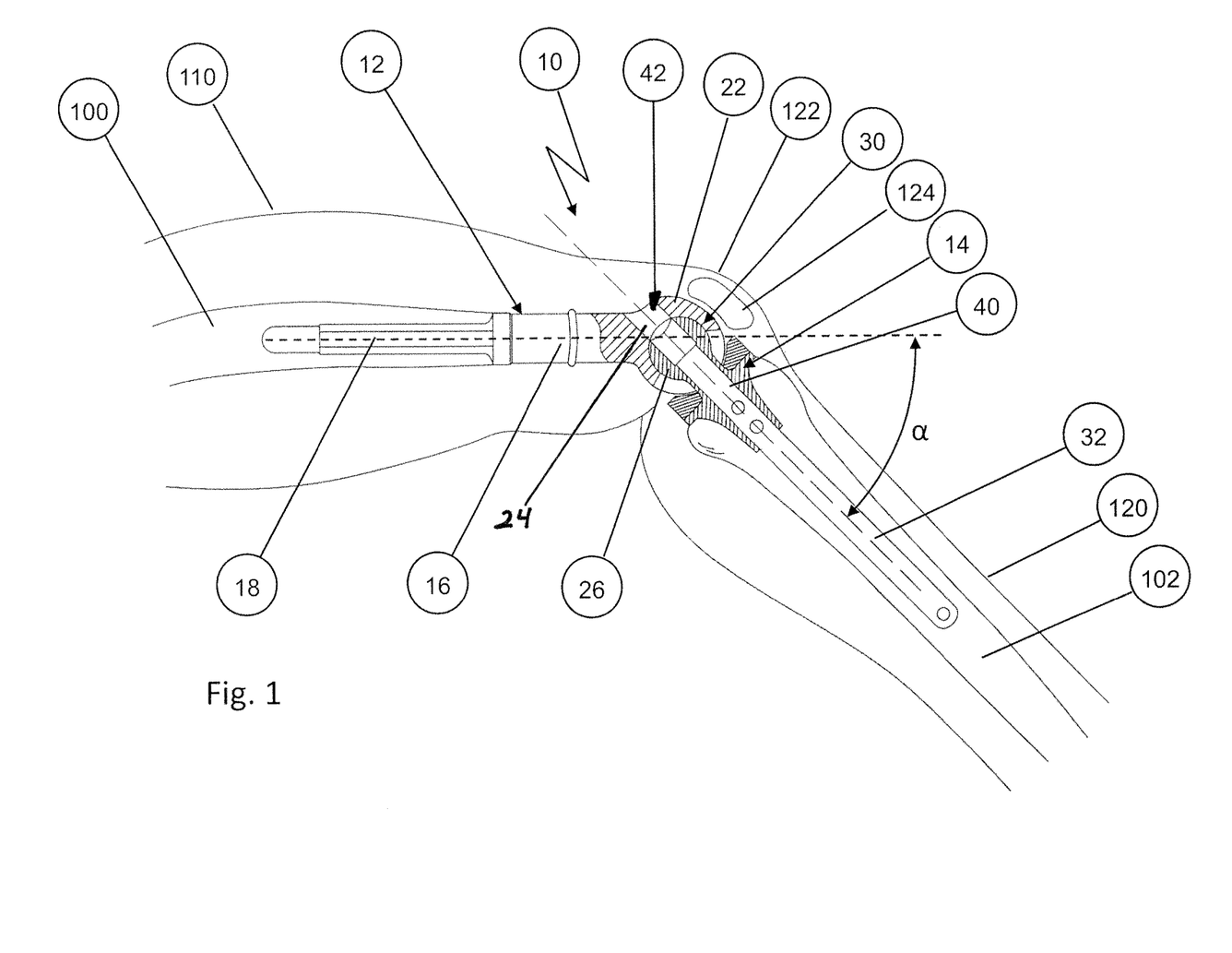
FIG. 1 is a schematic cross-sectional view in the sagittal plane of a first embodiment of an implantable prosthesis for replacing a human knee joint.

FIG. 1 is a schematic cross-sectional view in the sagittal plane of a first embodiment of an implantable prosthesis 10 for replacing a human knee joint. The prosthesis 10 includes a femoral prosthetic element 12, which is anchored by means of a femoral shaft anchoring part 18 in the femur 100 of a thigh 110 of a person.

The femoral prosthetic element 12 is implanted following resection of a tumor in the distal femur 100, the shaft of the femur 100 being partially replaced by a femoral shaft replacement 16, depending on the size of the tumor. Depending on the required length, the prosthetic element 12 can consist of one component or in a modular manner of a plurality of components.

A tibial prosthetic element 14 is anchored by means of a tibial shaft anchoring part 32 in the tibia 102 of the lower leg 120 and can likewise be of modular construction or consist of only one part. The prosthetic elements 12, 14 are articulated with one another by means of a joint device 30 so that the lower leg 120 is able to move relative to the thigh 110 in a manner corresponding to a knee bend.

The joint device 30 includes a joint head 22, which is fixed to the distal end of the femoral prosthetic element 12 and in which a joint element 26 connected to the proximal end of the tibial prosthetic element 14 is rotatably mounted.

The joint head 22 can be connected to the femoral prosthetic element 12 by screwing, welding, adhesive bonding or the like. The joint element 26 can be connected to the prosthetic element 14 in the same manner. The prosthetic element 12 and the joint head 22 can, however, also be produced from one piece as one part, as can the joint element 26 and the prosthetic element 14.

Figure 2:
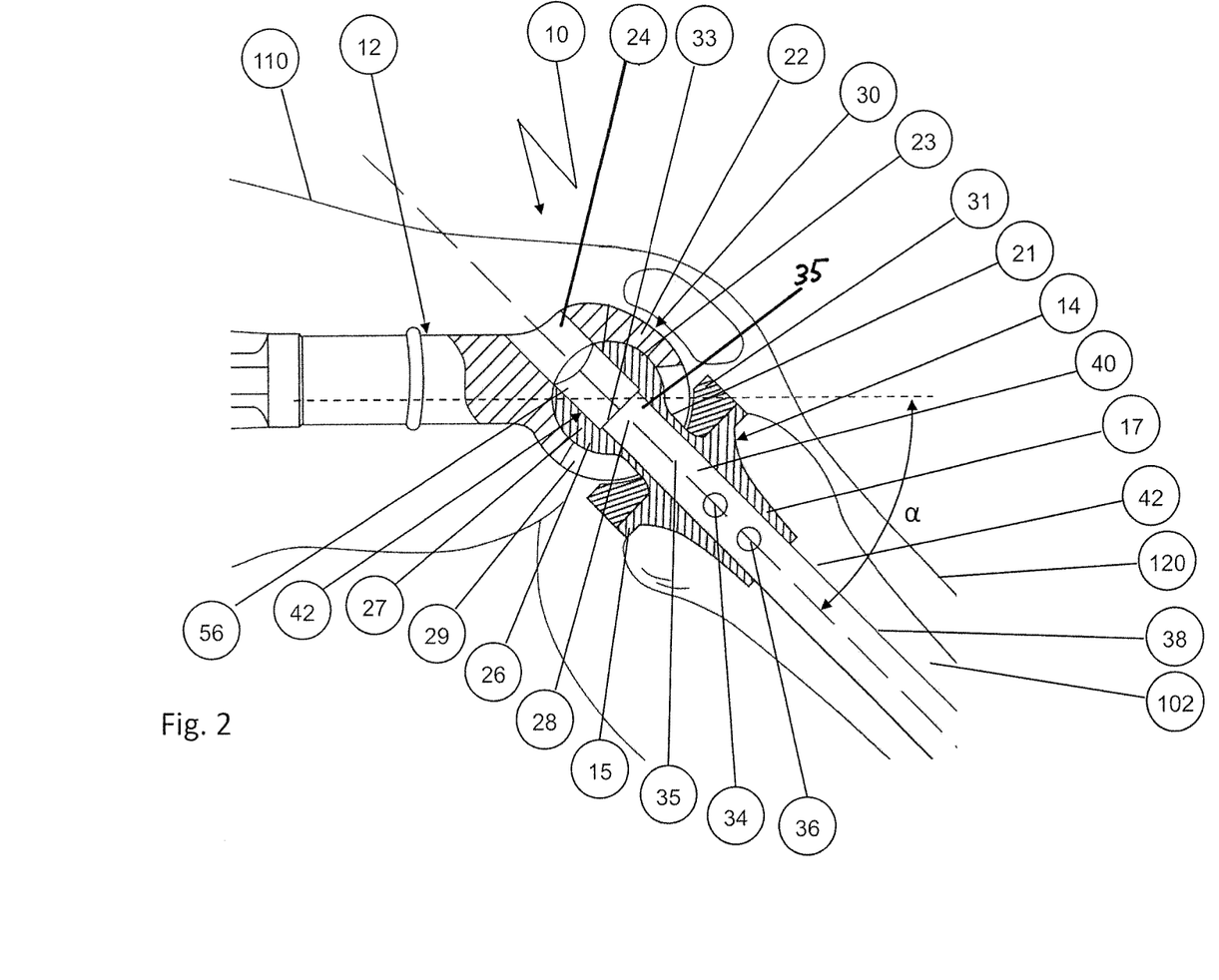
FIG. 2 is a more detailed partial view of the form of the prosthesis of FIG. 1.

The form of the prosthesis 10 of FIG. 1 is shown in greater detail in FIG. 2. In the functional position shown in FIG. 1, the lower leg 102 is bent downwards relative to the thigh 110 at an angle α from an extended position of the knee. The angle α is from 20° to 90°, preferably from 30° to 60°. In a particularly preferred embodiment, the angle α is from 30° to 45°.

In the joint head 22 a cylindrical interior space 23 is formed which opens obliquely upwards in the direction of the upper side of the thigh 110 via a passage 24 having a circular cross section, the angle between the central axis of the passage 24 and the central axis of the prosthetic element 12 corresponding substantially to the angle α. The joint element 26 having a cylindrical head portion 27 is pivotably mounted in the interior space 23. A foot portion 21 extends from the head portion 27 through a recess 29 in the joint head 22 in the direction of the tibial prosthetic element 14. The recess 29 is diametrally opposite the passage 24 with respect to the central axis of the head portion 27 and of the interior space 23 and is of such a size that the joint element 26 is able to pivot sufficiently for all knee bends without the movement of the foot portion 21 in the recess 29 being impeded.

The tibial prosthetic element 14 is inserted into and fixed in the proximal end of the tibia 102 close to the joint by means of a fixing projection 17 which tapers in the distal direction, and it includes a collar portion 15 which rests on the proximal end of the tibia 102 after the prosthetic element 14 has been inserted. The distal end face of the foot portion 21 of the joint element 26 is fixedly connected to the tibial prosthetic element 14 and has a central through-opening 40 of circular cross section which, in the functional position, extends coaxially with the passage 24 through the collar portion 15 and the fixing projection 17. A through-bore 28 of circular cross section passes through the joint element 26, which through-bore likewise extends coaxially with the passage 24 in the functional position.

In the functional position shown in FIGS. 1 and 2, the passage 24 and the through-bore 28 together form a guide channel 42 of circular cross section, which is in connection with the through-opening 40 in the prosthetic element 14. The through-bore 28 has a distal portion 35 which is connected to the through-opening 40 and has the same diameter as the through-opening. The distal portion 35 is advantageously followed by a proximal widened portion 56 of the through-bore 28, which in the functional position shown in FIG. 2 is aligned and in connection with the passage 24. A step 33 is thereby formed in the joint element 26 between the widened portion 56 and the portion 35 remote from the joint.

In the region of the fixing projection 17 transverse bores 34, 36 are provided in the prosthetic element 14 which are spaced apart from one another in the axial direction and pass through the wall of the fixing projection 17. Fixing pins for fixing a tibial shaft anchoring part 32 or an intramedullary lengthening nail 80, both to the fixing projection 17 and to the tibia 102, can be guided through the transverse bores 34, 36.

To the proximal surface of the collar portion 15 there is fixed a slide 31 on which the joint head 22 slides when the knee is moved, in order to avoid wear.

Figure 3:
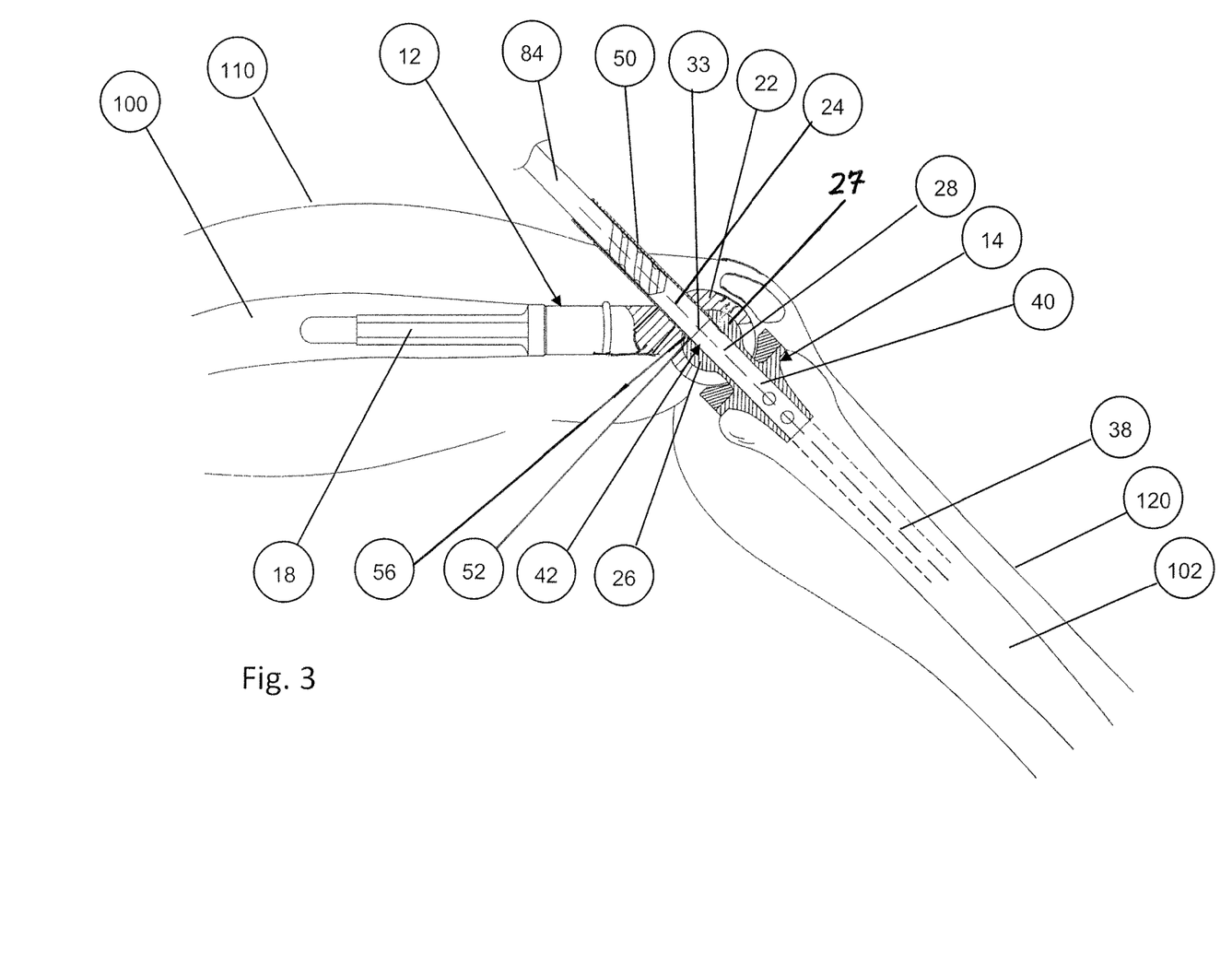
FIG. 3 is a schematic cross-sectional view in the sagittal plane of the prosthesis of FIG. 1 with a guide sleeve inserted into a joint device, through which guide sleeve a tool, for example a cutter, is introduced.

FIG. 3 shows the insertion of a guide sleeve 50 through the passage 24 into the widened portion 56 of the through-bore 28. The through-bore 28 and the through-opening 40 are always arranged coaxially with one another because the joint element 26 is fixedly connected to the prosthetic element 14 or forms a part therewith. When the lower leg 120 is pivoted by the angle α (see FIG. 2) with respect to the thigh 110 from an extended knee position into the functional position, the passage 24 in the joint head 22 is in alignment with the through-opening 40 and the through-bore 28 and forms the guide channel 42 with the through-bore 28. In this position, a guide sleeve 50 is introduced via a small skin incision after longitudinal incision of the quadriceps tendon via a dilator (not shown) and is inserted with an engagement end 52 through the passage 24 into the widened portion 56 of the through-bore 28, until the engagement end 52 sits on the step 33. The outside diameter of the guide sleeve 50 corresponds to the inside diameter of the widened portion 56. The inside diameter of the guide sleeve 50 is equal to the inside diameter of the distal portion 35 and of the through-opening 40.

Insertion of the engagement end 52 of the guide sleeve 50 into the widened portion 56 in the joint element 26 prevents the joint element 26 from rotating relative to the joint head 22. As is shown in FIG. 3, a tool, for example a cutter 84, whose outside diameter corresponds to the inside diameter of the guide sleeve 50, can then be guided through the passage 24, the through-bore 28 and the through-opening 40 in order to form a drill channel 38 in the tibia 102. Other tools, such as, for example, drills, or shaft anchoring parts or intramedullary lengthening nails can also be inserted or removed through the guide sleeve.

Figure 4:
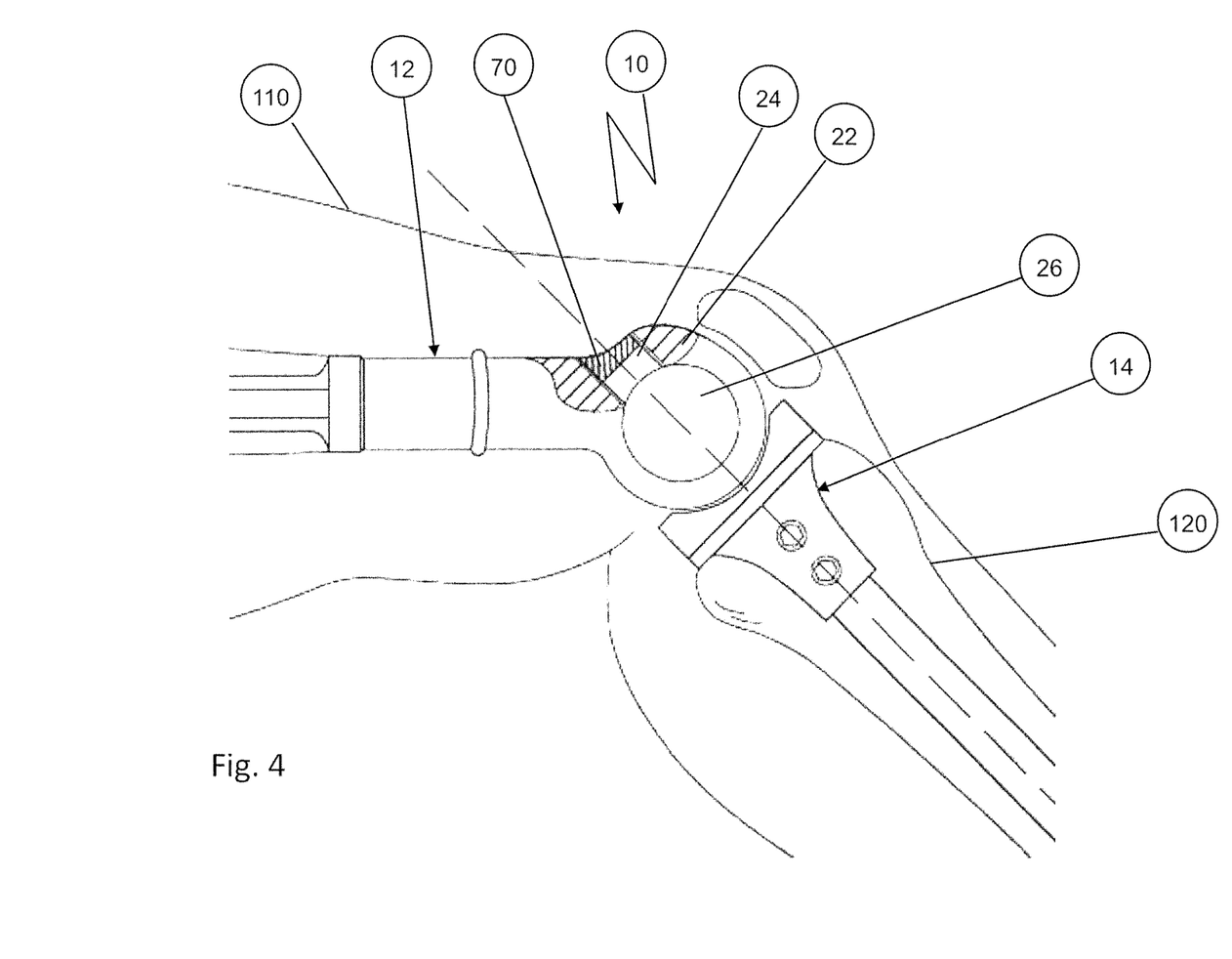
FIG. 4 shows the embodiment of the prosthesis of FIG. 1 having a plug arranged in a passage in the femoral joint head.

FIG. 4 shows that, after a tool has been used or after an intramedullary lengthening nail or a shaft anchoring part has been inserted or removed, the passage 24 can be closed by a plug 70, the outside surface of which is flush with the surface of the femoral prosthetic component. The plug is preferably made of PTFP, PVC or PEEK.

Figure 5:
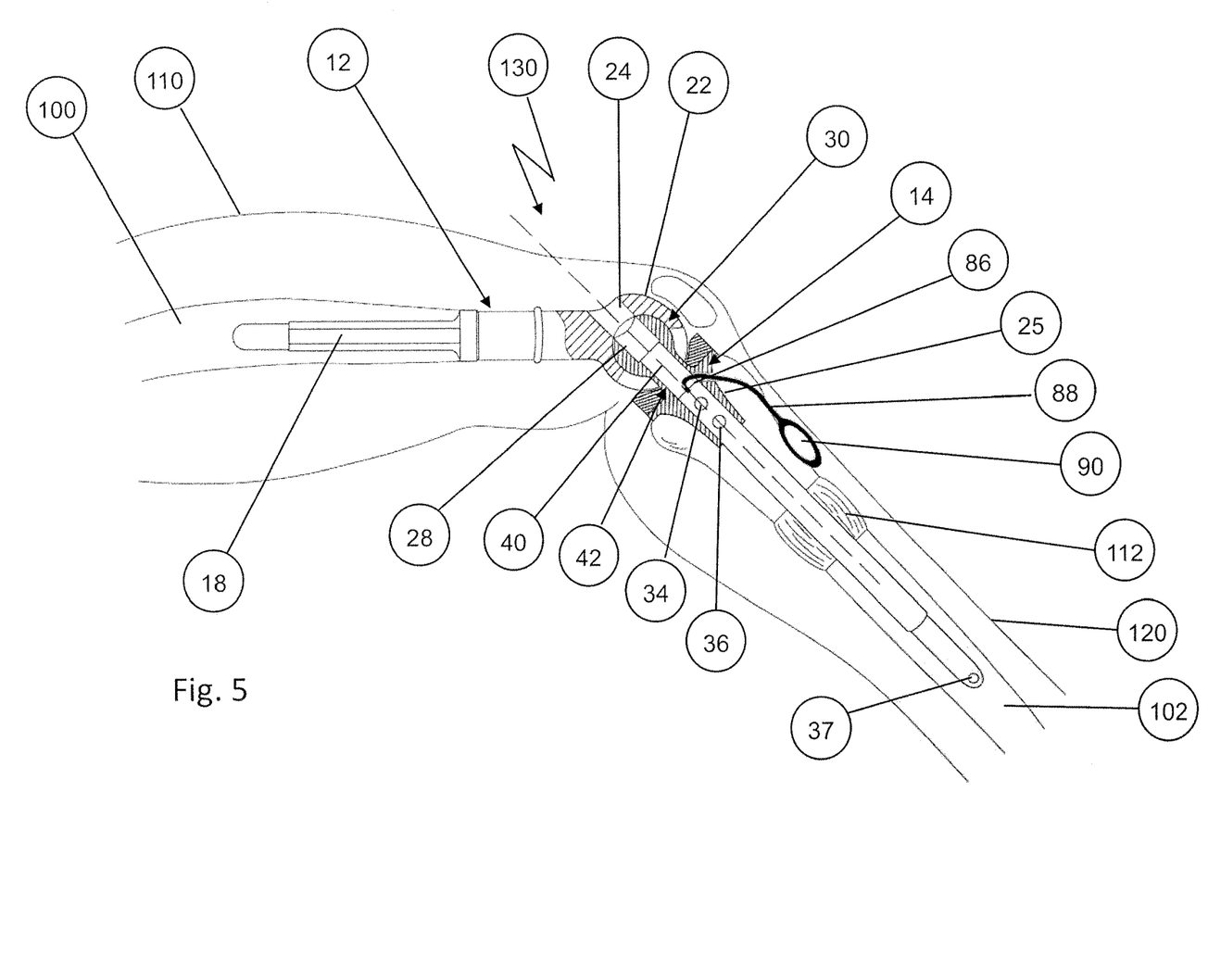
FIG. 5 is a schematic cross-sectional view in the sagittal plane of a second embodiment of an implantable prosthesis for replacing a human knee joint, having an intramedullary lengthening nail arranged in the tibia.

The second embodiment of the prosthesis 130 shown in FIG. 5 corresponds substantially to the embodiment of FIGS. 1 to 4 and differs substantially only in that a lateral opening 86 passes through the wall of the fixing projection 25 of the tibial prosthetic element 14. An intramedullary lengthening nail 80 is guided through the passage 24, the through-bore 28 and the through-opening 40, which intramedullary lengthening nail can be lengthened by means of a motor so that bone lengthening by the callus distraction method is possible and new bone tissue 112 can form in the distraction gap of the fractured tibia. For controlling the motor, a cable 88 connected to the intramedullary lengthening nail 80 passes outwards through the lateral opening 86. An antenna 90 is provided at the free end of the cable 88. The intramedullary lengthening nail 80 is fixed to the prosthetic element 14 and possibly also to the proximal tibia by bolts which pass through the transverse bores 34, 36, and is additionally fixed to the distal tibia by bolts which pass through a transverse bore 37.

Figure 6:
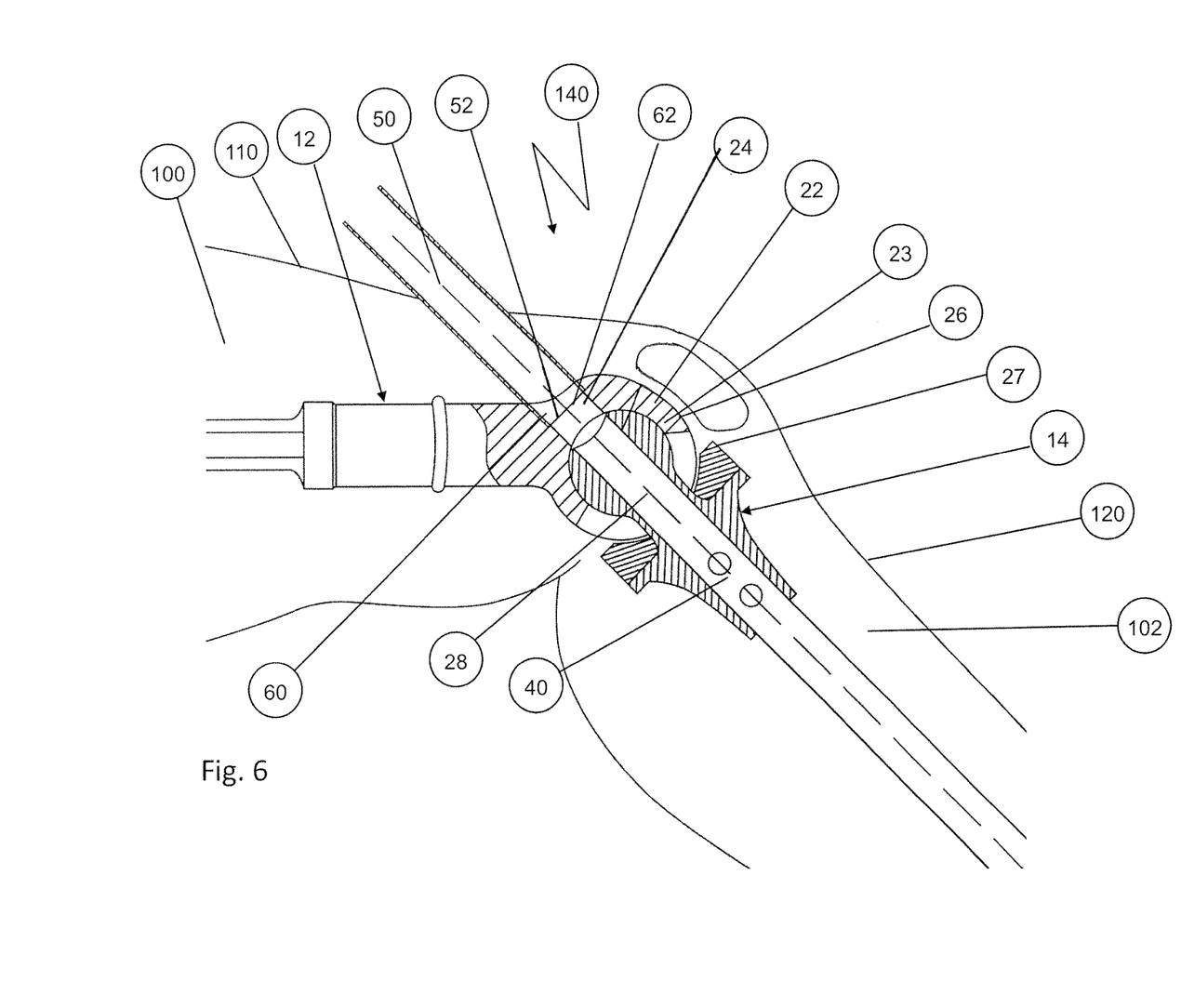
FIG. 6 is a schematic cross-sectional view in the sagittal plane of a third embodiment of an implantable prosthesis for replacing a human knee joint, having a guide sleeve inserted only in the femoral joint head.

The embodiment of the prosthesis 140 shown in FIG. 6 differs from the embodiment shown in FIG. 2 in that the passage 28 has a constant diameter, which corresponds to the diameter of the through-opening 40. The passage 24 has a proximal widened portion 60, which opens on the outside of the joint head 22. A step 62 is thereby formed. A guide sleeve 50 is inserted so that it rests with its engagement end 52 on the step 62.

In the embodiments shown, the joint head 22 has a cylindrical interior space 23 and the head portion 27 of the joint element 26 is likewise cylindrical in the distal region, the outside diameter of the head portion 27 corresponding to the diameter of the interior space 23, so that a hinge connection is formed. Different joint connections between the femoral prosthetic element 12 and the tibial prosthetic element 14 are also possible, however. For example, the interior space 23 can be spherical and the head portion 27 can be spherical, in order to permit three-dimensional movements.

It is also not absolutely essential that the guide channel 42 passes through the joint device 30. In principle, it is also conceivable for the guide channel 42 to extend laterally outside the joint device 30. The joint device 30 can also have two or more elements arranged spaced apart along the pivot axis. The guide channel 42 could then be arranged between two of those elements.

The invention claimed is:

1. An implantable prosthesis for replacing a human knee joint, comprising:
a femoral prosthetic element and a tibial prosthetic element which are articulated with one another by means of a joint device for the purpose of executing a knee bend, the tibial prosthetic element having a through-opening for the passage of a tool, a rod-like tibial shaft anchoring part or an intramedullary lengthening nail,
wherein the joint device is designed to form a guide channel for the passage of the tool, the rod-like tibial shaft anchoring part or the intramedullary lengthening nail from outside, which guide channel is in alignment with the through-opening and is in connection therewith when the tibial prosthetic element and the femoral prosthetic element are arranged at a predetermined angle relative to one another in a functional position corresponding to a knee bend, and
wherein the joint device comprises a joint head which is connected to the femoral prosthetic element and has an interior space in which a joint element connected to the tibial prosthetic element is rotatably guided for guiding the knee bend, a passage opening into the interior space being formed in the joint head and a through-bore being formed in the joint element, the passage and the through-bore being in alignment with one another in the functional position to form the guide channel.

2. The prosthesis according to claim 1, wherein the passage and the through-bore have a circular cross section and the same diameter.

3. The prosthesis according to claim 1, wherein the passage and the through-bore have a circular cross section, the diameter of the passage at an outwardly opening, widened portion being larger than the diameter of the through-bore, so that a guide sleeve whose inner diameter corresponds to the diameter of the through-bore can be inserted into the passage.

4. The prosthesis according to claim 3, wherein means for releasably fixing the guide sleeve in the passage are provided on the guide sleeve and the passage.

5. The prosthesis according to claim 1, wherein the passage and the through-bore have a circular cross section, the diameter of the passage being larger than the diameter of a first portion of the through-bore and the through-bore having at its end facing the passage a widened portion with a widened diameter corresponding to the diameter of the passage, so that a guide sleeve whose inner diameter corresponds to the diameter of the first portion of the through-bore can be inserted into the passage in the functional position so that the guide sleeve engages in the widened portion with an engagement end to block an unintentional joint movement.

6. The prosthesis according to claim 5, wherein means for releasably fixing the guide sleeve in the through-bore are provided on the guide sleeve and the through-bore.

7. The prosthesis according to claim 1, wherein a plug is releasably arranged in the passage, the outer surface of which plug is flush with the surface of the femoral prosthetic element.

8. The prosthesis according to claim 7, wherein the plug is made of PTFE, PVC or PEEK.

9. The prosthesis according to claim 1, wherein, in the tibial prosthetic element, at least one lateral transverse bore is formed through which transverse screws or transverse bolts for interlocking connection of the tibial prosthetic element to a shaft anchoring part, an intramedullary lengthening nail and/or the tibia can be inserted.

10. The prosthesis according to claim 1, wherein, in the tibial prosthetic element, a lateral opening is provided for the passage of a cable which can be connected to an intramedullary lengthening nail.

11. The prosthesis according to claim 1, wherein the guide channel passes through the joint device.

12. The prosthesis according to claim 1, wherein the guide channel runs centrally or non-centrally through the joint device.

13. The prosthesis according to claim 1, wherein the femoral prosthetic element forms a part with the joint head.

14. The prosthesis according to claim 13, wherein the tibial prosthetic element forms a part with the joint element.

15. The prosthesis according to claim 1, wherein the tibial prosthetic element forms a part with the joint element.

16. The prosthesis according to claim 1, wherein the predetermined angle of a knee bend is from 30° to 60° from an extended position of the knee.

17. The prosthesis according to claim 1, wherein the predetermined angle of a knee bend is from 30° to 45° from an extended position of the knee.

18. The prosthesis according to claim 1, wherein the predetermined angle of a knee bend is from 20° to 90° from an extended position of the knee.

* * * * *